(12) United States Patent
Kang et al.

(10) Patent No.: US 9,744,117 B2
(45) Date of Patent: Aug. 29, 2017

(54) COSMETICS COMPRISING COSMETIC COMPOSITIONS IMPREGNATED IN HYDROPHOBIC POLYMER FOAM

(71) Applicant: LG HOUSEHOLD & HEALTH CARE LTD., Seoul (KR)

(72) Inventors: Sung-Soo Kang, Daejeon (KR);
Kwang-Ho Oh, Daejeon (KR);
Gap-Joo Lee, Daejeon (KR);
Sang-Wook Park, Daejeon (KR);
Kyong-Seob Kim, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 15/031,935

(22) PCT Filed: Nov. 11, 2015

(86) PCT No.: PCT/KR2015/012132
§ 371 (c)(1),
(2) Date: Apr. 25, 2016

(87) PCT Pub. No.: WO2016/137087
PCT Pub. Date: Sep. 1, 2016

(65) Prior Publication Data
US 2016/0367469 A1    Dec. 22, 2016

(30) Foreign Application Priority Data

Feb. 27, 2015 (KR) .................. 10-2015-0028454
Jun. 8, 2015 (KR) .................. 10-2015-0080751

(51) Int. Cl.
*A61K 8/49* (2006.01)
*A61K 8/81* (2006.01)
*A61Q 17/04* (2006.01)
*A61K 8/02* (2006.01)
*A61K 8/04* (2006.01)
*A61K 8/06* (2006.01)
*A61K 8/37* (2006.01)
*A61K 8/41* (2006.01)

(52) U.S. Cl.
CPC .............. *A61K 8/8194* (2013.01); *A61K 8/02* (2013.01); *A61K 8/04* (2013.01); *A61K 8/046* (2013.01); *A61K 8/064* (2013.01); *A61K 8/37* (2013.01); *A61K 8/41* (2013.01); *A61Q 17/04* (2013.01); *A61K 2800/54* (2013.01)

(58) Field of Classification Search
None
See application file for complete search history.

(56) References Cited

U.S. PATENT DOCUMENTS

| | | | |
|---|---|---|---|
| 4,517,313 A | 5/1985 | Natatami | 521/51 |
| 8,784,854 B2 * | 7/2014 | Choi | A61Q 1/02 424/401 |
| 2009/0258964 A1 * | 10/2009 | Omura | A61K 8/042 523/105 |
| 2015/0117931 A1 | 4/2015 | Jung et al. | |
| 2015/0118269 A1 | 4/2015 | Choi et al. | |
| 2015/0166253 A1 | 6/2015 | Nomura et al. | B65D 83/14 |

FOREIGN PATENT DOCUMENTS

| | | | |
|---|---|---|---|
| JP | H58-216005 | 12/1983 | A45D 34/04 |
| JP | H07-313248 | 12/1995 | A45D 34/04 |
| KR | 10-2009-0100643 | 9/2009 | A61K 8/87 |
| KR | 10-2013-0116182 | 10/2013 | C08J 9/00 |
| KR | 10-2013-0116205 | 10/2013 | A61K 8/67 |
| KR | 10-2015-0011887 | 2/2015 | A61K 8/89 |
| WO | WO 2013-147064 | 10/2013 | B65D 83/44 |

OTHER PUBLICATIONS

International Search Report (ISR) and Written Opinion (WO) dated Feb. 2, 2016 in PCT/KR2015/012132.
Statement the English Translation of Office Action and Notice of Allowance of Korean Patent Application is Accurate; Office Action dated Jul. 24, 2015 in Korean Patent Application No. 10-2015-0080751 with English translation; and Notice of Allowance dated Oct. 8, 2015 in Korean Patent Application No. 10-2015-0080751 with English translation.
Allowed Claims in Korean Patent Application No. 10-2015-0080751.

* cited by examiner

*Primary Examiner* — Susan Tran
(74) *Attorney, Agent, or Firm* — Harness, Dickey & Pierce, P.L.C.

(57) ABSTRACT

The present disclosure relates to cosmetics including a foam for cosmetic composition impregnation including natural rubber (NR) and hydrophobic polymer as a polymer substrate for making the foam, and a cosmetic composition including an organic ultraviolet (UV) blocking component, that is impregnated in the foam. The present disclosure has a reduction in amount of the organic UV blocking component adsorbed to the impregnation material, and can obtain an excellent UV blocking effect.

6 Claims, No Drawings

COSMETICS COMPRISING COSMETIC COMPOSITIONS IMPREGNATED IN HYDROPHOBIC POLYMER FOAM

CROSS-REFERENCE TO RELATED APPLICATIONS

This application is a national phase application of PCT Application No. PCT/KR2015/012132, filed on 11 Nov. 2015, which claims benefit of Korean Patent Application Nos. KR 10-2015-0080751 filed 8 Jun. 2015 and KR 10-2015-0028454 filed 27 Feb. 2015. The entire disclosures of the applications identified in this paragraph are incorporated herein by references.

FIELD

The present disclosure relates to cosmetics including an impregnation material, and more particularly, to cosmetics including an impregnated cosmetic composition containing an ultraviolet (UV) blocking agent, in which an organic UV blocking component included in the cosmetic composition is not adsorbed to an impregnation material and its content can be uniformly maintained.

BACKGROUND

An ultraviolet (UV) blocking agent used in a cosmetic composition can be largely classified into an organic UV blocking agent and an inorganic UV blocking agent according to its properties. Of them, the organic UV blocking agent blocks UV rays by absorbing the energy of UV rays that reach on the skin, and it has advantages over the inorganic UV blocking agent—it is less susceptible to whitening, it can effectively block UV rays when applied to the skin because it is applied to the skin in molecular state, and it can be developed in light formulation, such as in the form of milk type, gel, and lotion as well as in the form of cream or foundation.

Hydrophobic polymer foams such as NBR and SBR are being widely used as a material for cosmetic composition impregnation because of having good wear resistance or oil resistance, but their disadvantage is low workability.

To solve the problem of the hydrophobic polymer foams, natural rubber (NR) is used for a polymer substrate for making a foam. Due to its good compatibility with hydrophobic polymers such as polyethylene, polypropylene, polystyrene, and polyester, formed by polymerization of hydrophobic monomers such as ethylene, propylene, styrene, and ester, NR is widely used as a material for blending with other hydrophobic polymer when making a foam. Particularly, when it is used for cosmetic composition impregnation, NR has advantages—it feels good and has good mechanical properties such as wear resistance. However, the present inventors found the fact that an adsorption problem of an oil soluble organic UV blocking agent occurs in an impregnation material used together with NR. To solve the problem, an attempt is made to solve the adsorption problem of an oil soluble organic UV blocking agent that occurs when both NR and NBR are used for a polymer substrate.

DISCLOSURE

Technical Problem

To solve the above problem, the present disclosure identified a combination of materials having a low ability to adsorb an organic ultraviolet (UV) blocking agent and completed the present invention.

The present disclosure is directed to provide cosmetics including an impregnation material that can resolve the limitation in use of an organic UV blocking agent and solve an adsorption problem of an UV blocking agent to an impregnation material.

Technical Solution

To achieve the above object, the present inventors have conducted research to find a solution to an adsorption problem of an organic ultraviolet (UV) blocking component to an impregnation material including natural rubber (NR) for years, and finally completed the present invention.

According to an embodiment of the present disclosure, there are provided cosmetics including a foam for cosmetic composition impregnation including NR and hydrophobic polymer for a polymer substrate for making the foam, and a cosmetic composition including an organic UV blocking component that is impregnated in the foam.

In the cosmetics including the impregnation material (or the foam for impregnation) using hydrophobic polymers, to minimize the adsorption of the organic UV blocking component included in the cosmetic composition, research has been done to find an optimum combination ratio of the hydrophobic polymers and the NR included in the polymer substrate of the foam for years, and the present invention was made.

The term 'foam for impregnation' or 'impregnation material' used herein refers to a substance having pores inside such as a porous sponge, and includes a foam in narrow sense. The foam for impregnation or impregnation material refers to a foamed structure having pores formed using a foaming agent, but a naturally formed porous material with no foaming process due to the properties of the NR may be included in the impregnation material of the present disclosure.

The present inventors ascertained that particularly NR is advantageous in manufacturing a foam due to good compatibility with other hydrophobic polymers, but difficult to use it for cosmetic composition impregnation due to having a high ability to adsorb an oil soluble organic UV blocking agent.

According to an embodiment of the present disclosure, the foam that can be used as the impregnation material to achieve the object of the present disclosure includes hydrophobic monomer polymers, such as, polymers or copolymers of styrene, butadiene, chloroprene, acrylonitrile, isoprene, isobutylene, ethylene and propylene, singly or in combination, and the polymers include, for example, styrene-butadiene rubber (SBR), butadiene rubber (BR), acrylonitrile-butadiene rubber (NBR), acrylonitrile-butadiene-styrene (ABS), polyethylene (PE), polyvinyl alcohol (PVA), and ethylene vinyl acetate (EVA).

Preferably, the foam that can be used as the impregnation material includes blends of NR and at least one hydrophobic polymer selected from the group consisting of Nitrile rubber (NBR), Styrene-butadiene rubber (SBR) and butadiene rubber (BR), but the hydrophobic polymer that can be blended with the NR is not limited to a particular type.

The present inventors provide the foam in which the polymer substrate of the blend of the NR and the hydrophobic polymer is used as the impregnation material for cosmetic composition impregnation.

The impregnation material for cosmetic composition impregnation included in an embodiment of the present disclosure includes the NR in an amount of 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.5 wt % or less, 0.4 wt % or less, 0.3 wt % or less, 0.2 wt % or less, 0.15 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less, 0.01 wt % or less, 0.001 wt % or less, 0.0001 wt % or less, and preferably 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.5 wt % or less, 0.4 wt % or less, 0.3 wt % or less, 0.2 wt % or less, 0.15 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less, 0.01 wt % or less, 0.001 wt % or less, 0.0001 wt % or less, more preferably 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.5 wt % or less, 0.4 wt % or less, 0.3 wt % or less, 0.2 wt % or less, 0.15 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less, 0.01 wt % or less, 0.001 wt % or less, 0.0001 wt % or less, and even more preferably 5 wt % or less, 4 wt % or less, 3 wt % or less, 2 wt % or less, 1 wt % or less, 0.5 wt % or less, 0.4 wt % or less, 0.3 wt % or less, 0.2 wt % or less, 0.15 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less, 0.01 wt % or less, 0.001 wt % or less, 0.0001 wt % or less, per the total weight of the polymer substrate for making the impregnation material (i.e., the blend of the NR and the hydrophobic polymer, including both the NR and the hydrophobic polymer).

The polymer substrate for making the impregnation material (i.e., the blend of the NR and the hydrophobic polymer, including both the NR and the hydrophobic polymer) includes both the NR and the hydrophobic polymer, and preferably, the use of the hydrophobic polymer alone for the polymer substrate is not included in the scope of the present disclosure and the hydrophobic polymer may be present in at least 0.00001 wt % or more per the total weight of the blend of the NR and the hydrophobic polymer.

When the content ratio of the NR included in the polymer substrate exceeds the above range, the degree of adsorption of the organic UV blocking agent increases, which renders unsuitable as a cosmetic composition impregnation material.

The term 'natural rubber (NR)' used herein refers to general natural rubber or modified natural rubber. The general natural rubber includes any substance known as natural rubber, and there is no particular limitation on the place of origin. The natural rubber includes cis-1,4-polyisoprene preponderantly, but may include trans-1,4-polyisoprene according to the required properties. Thus, the natural rubber includes not only natural rubber including cis-1,4-polyisoprene preponderantly, but also natural rubber including trans-1,4-isoprene preponderantly, for example, balata, a kind of Sapotaceae rubber in South America. The modified natural rubber refers to any modified or purified product of the general natural rubber. For example, the modified natural rubber includes epoxidized natural rubber (ENR), deproteinised natural rubber (DPNR), and hydrogenated natural rubber.

A method of making the foam using the blend of the NR and the hydrophobic polymer includes general methods used in the industries who make foams. Catalysts and foaming agents used to make the foam include general materials used in the art, and are not limited to a particular type. For example, the foam may be made with reference to the methods disclosed in Patent Literature U.S. Pat. No. 4,517,313 and Non-Patent Literature Oertel, G. Polyurethane Handbook. Second ed. Munich: Carl Hanser Publishers, 1993.

The porous foam according to an embodiment of the present disclosure may be formed by foaming polymers including hydrophobic monomers. By controlling the foaming process, the pore size, porosity and pore distribution of the foam may be controlled. According to the general industry, foaming of polymers can be achieved by optimally controlling an amount and type of the foaming agent, an injection amount of air for foaming and the foaming temperature and the type of the hydrophobic monomers (particularly, the length of a main chain and a branched chain of the monomers) in the manufacture, and this adjustment is obvious to those skilled in the art.

The impregnation material of the present disclosure is preferably used for cosmetic composition impregnation.

The term 'impregnation' used herein is used as the general meaning used in the industry who produces cosmetic compositions, and specifically, refers to immersing contents in a material having pores inside such as a sponge.

The term 'immersion' used herein refers to holding and storing any material (e.g., liquid-type cosmetics). For example, the applications include, but are not limited to, cosmetics that include a flowable cosmetic composition and can be applied on the skin using a separate tool.

The flowable cosmetic composition includes skin, toner, lotion, cream, gel, liquid foundation, gel-type foundation, makeup primer, makeup base, skin cover, lip gloss, eye shadow, blusher and concealer, and there is no particular limitation on the formulation. For example, a low viscosity cosmetic composition of water-in-oil type and oil-in-water type may be impregnated in the impregnation material.

In the present disclosure, preferably the cosmetic composition including an UV blocking component is impregnated, and preferably the cosmetic composition including an organic UV blocking component is impregnated.

When the cosmetic composition including the organic UV blocking component is impregnated in the NR foam, if an oil soluble material is adsorbed to the impregnation material, the intrinsic object of the cosmetic composition cannot be achieved, causing the UV blocking performance to degrade.

The organic UV blocking component includes all organic UV blocking components generally known in the art, for example, ethylhexylmethoxycinnamate, ethylhexylsalicylate, octocrylene, isoamyl-P-methoxycinnamate, butyl-methoxydibenzoylmethane, homosalate, bis-ethylhexyloxyphenolmethoxyphenyltriazine, ethylhexyltriazone, diethylaminohydroxybenzoylhexylbenzoate, polysilicone-15, cinoxate, 4-methylbenzylidene camphor, and paba derivatives such as paba(para-aminobenzoic acid), and/or glyceryl para-aminobenzoate, ethylhexyl dimethyl paba, and preferably, the organic UV blocking component includes ethylhexylmethoxycinnamate, ethylhexylsalicylate, octocrylene or mixtures thereof.

Advantageous Effects

The present disclosure can solve an adsorption problem of an organic ultraviolet (UV) blocking component to an impregnation material that is problematic for cosmetics including an impregnated cosmetic composition containing the organic UV blocking component.

The present disclosure can obtain an excellent UV blocking effect.

BEST MODE

Hereinafter, the present disclosure will be described in detail through the following embodiments. However, the embodiments according to the present disclosure may be modified in many different forms, and the scope of the present disclosure shall not be construed as being limited to the embodiments mentioned below. The embodiments of the present disclosure are provided for illustration to help a full understanding of the present disclosure.

<Preparation of Water-in-Oil Type Foundation>

Water-in-oil type foundations of composition examples 1, 2 and 3 were prepared as below.

Oil phase components and a thickening agent were put in an oil phase tank and heated to 80° C. to turn into a uniform state, and a pigment was added and dispersed. Water phase components were put in a water phase tank and heated to 80° C. to completely dissolve the raw materials, and then were added to the oil phase tank containing the dispersed pigment, followed by emulsification using a homo mixer to prepare a low viscosity ultraviolet (UV) blocking emulsion. A 40 ml stabilization container was filled with the contents and kept at a 25° C. chamber for one day or longer, and after operation of Brookfield LVII viscometer at 30 rpm for 1 minute using spindle 4, when viscosity was measured at 25° C., the viscosity was in the range of 3,000~5,000 cps. The following Table 1 is a table showing compositions for producing foundation for impregnation.

TABLE 1

| Classification | Name of raw material (wt %) | Composition example 1 | Composition example 2 | Composition example 3 |
|---|---|---|---|---|
| Oil phase component | Cyclopentasiloxane | 30.0 | 30 | 30 |
| | Ethylhexylmethoxycinnamate | 5.0 | — | — |
| | Ethylhexylsalicylate | — | 5.0 | — |
| | Octocrylene | — | — | 5.0 |
| | Dimethicone | 3.0 | 3.0 | 3.0 |
| | Caprylic/capric triglyceride | 3.0 | 3.0 | 3.0 |
| | PEG-10 dimethicone | 3.0 | 3.0 | 3.0 |
| | Sorbitan sesquioleate | 1.0 | 1.0 | 1.0 |
| | Disteardimonium hectorite | Optimum amount | Optimum amount | Optimum amount |
| Pigment | Titanium dioxide | 5.0 | 5.0 | 5.0 |
| | Mica | 3.0 | 3.0 | 3.0 |
| | Yellow iron oxide | 1.0 | 1.0 | 1.0 |
| | Red iron oxide | 0.2 | 0.2 | 0.2 |
| | Black iron oxide | 0.1 | 0.1 | 0.1 |
| Water phase | Water | to 100 | to 100 | to 100 |
| | Dipropylene glycol | 5.0 | 5.0 | 5.0 |
| | Salt | 1.0 | 1.0 | 1.0 |

<Determination of Adsorption Ratio of Organic UV Blocking Agent Component for Each Ratio of NR, NBR and SBR>

The foam for each ratio of NR, NBR and SBR was available from S&G (LG-latex #1001-1014), and tailored into a cylindrical shape having a diameter of 50 mm and a height of 10 mm, followed by impregnation with a cosmetic composition. After being kept at room temperature for 24 hours, foundation not impregnated into the sponge surface was removed, and the sponge was squeezed by hands to collect the foundation. The collected foundation solution was retained for the same time and measured by the following method.

20 mg of each of the foundation before impregnation into the sponge and the foundation collected from the sponge was dissolved in methanol to make 100 ml, which was passed through a 0.45 micrometer filtration membrane, followed by test using an ultraviolet absorption spectrometer according to liquid chromatography to determine a peak area AT of ethylhexylmethoxycinnamate (EHMC), ethylhexylsalicylate (EHS) and octocrylene (OC) and a peak area As of a reference standard, and a changed value before and after impregnation was analyzed.

(1) an amount of ethylhexylmethoxycinnamate (mg)=AT/As×an amount of ethylhexylmethoxycinnamate reference standard (mg)

(2) an amount of ethylhexylsalicylate (mg)=AT/As×an amount of ethylhexylsalicylate reference standard (mg)

(3) octocrylene (mg)=AT/As×an amount of octocrylene (mg)

The results are as shown in Table 2 and Table 3.

The following Table 2 shows a comparison of the degree of adsorption of the organic UV blocking agent for each content of NR and SBR.

TABLE 2

| Cosmetic composition | Example 1 Composition example 1 | Example 2 Composition example 2 | Example 3 Composition example 3 |
|---|---|---|---|
| Organic UV blocking agent | EHMC | EHS | OC |
| Before impregnation | 5.25 | 5.13 | 5.12 |
| NR/SBR (80/20) | 2.78 | 2.58 | 2.85 |
| NR/SBR (60/40) | 3.35 | 3.32 | 3.44 |
| NR/SBR (40/60) | 4.36 | 4.30 | 4.46 |
| NR/SBR (20/80) | 4.80 | 4.51 | 4.76 |
| NR/SBR (10/90) | 4.79 | 4.54 | 4.78 |
| NR/SBR (5/95) | 4.81 | 4.60 | 4.80 |
| NR/SBR (0/100) | 4.78 | 4.63 | 4.79 |

As can be seen from the above Table 2, examples 1-3 demonstrated the degree of adsorption of the organic UV blocking component changes depending on the content of NR used for the polymer substrate of the sponge.

Particularly, it was seen that when the NR ratio exceeds 20 wt %, the degree of organic UV adsorption was high.

When NR was absent, the degree of adsorption of the organic UV blocking component was not high, but the impregnation material felt bad and is very susceptible to wear, so it was relatively unsuitable for use of cosmetic composition impregnation as compared to the case where NR was present.

The following Table 3 shows a comparison of the degree of adsorption of the organic UV blocking agent for each content of NR and NBR.

TABLE 3

| Cosmetic composition | Example 4 Composition example 1 | Example 5 Composition example 2 | Example 6 Composition example 3 |
|---|---|---|---|
| Organic UV blocking agent | EHMC | EHS | OC |
| Before impregnation | 5.25 | 5.13 | 5.12 |
| NR/NBR (80/20) | 2.71 | 2.50 | 2.84 |
| NR/NBR (40/60) | 4.20 | 4.23 | 4.31 |
| NR/NBR (20/80) | 4.86 | 4.52 | 4.72 |
| NR/NBR (10/90) | 4.88 | 4.60 | 4.72 |

As can be seen from the results of Table 3 above, it was seen that when the NR ratio exceeds 20%, the degree of adsorption of the organic UV blocking agent increases, which renders unsuitable as products.

Similar to the case where SBR is used, in the case where NBR is used, when NR is absent, the degree of adsorption of the organic UV blocking component was not high, but the impregnation material felt bad and is very susceptible to wear, so it was relatively unsuitable for use of cosmetic composition impregnation as compared to the case where NR was present.

The following Table 4 shows a comparison of the degree of adsorption of the organic UV blocking agent for each content of NR and BR.

TABLE 4

| Cosmetic composition | Example 7 Composition example 1 | Example 8 Composition example 2 | Example 9 Composition example 3 |
|---|---|---|---|
| Organic UV blocking agent | EHMC | EHS | OC |
| Before impregnation | 5.25 | 5.13 | 5.12 |
| NR/BR (80/20) | 2.65 | 2.52 | 2.80 |
| NR/BR (40/60) | 4.22 | 4.25 | 4.30 |
| NR/BR (20/80) | 4.78 | 4.50 | 4.68 |
| NR/BR (10/90) | 4.80 | 4.67 | 4.72 |

Further, the foundation of composition example 1 was uniformly applied onto the artificial skin (vitroskin) using the NR/SBR (10/90) and NR/NBR (10/90) sponges impregnated therewith and left behind for 10 minutes, and sun protection factor (SPF) values were measured using an SPF measurement device (SPF-2905).

The results are as shown in Table 5.

TABLE 5

| Cosmetic composition | Composition example 1 SPF |
|---|---|
| Before impregnation | 41 |
| NR/SBR (10/90) | 37 |

TABLE 5-continued

| Cosmetic composition | Composition example 1 SPF |
|---|---|
| NR/NBR (10/90) | 38 |
| NR/BR (10/90) | 37 |

As can be seen from the Table 5 above, the impregnation material including less than 20% of NR had an improved degree of adsorption of the UV blocking component, and consequently, a high UV blocking effect of the impregnated cosmetic composition can be expected.

INDUSTRIAL APPLICABILITY

The cosmetics according to the present disclosure provide cosmetics that solved the adsorption problem of the organic ultraviolet (UV) blocking component to the impregnation material, involved in the cosmetics in which the cosmetic composition including the organic UV blocking component is impregnated in the foam.

What is claimed is:

1. A cosmetic comprising:
   a foam for cosmetic composition impregnation including natural rubber (NR) and a hydrophobic polymer as a polymer substrate for making the foam; and
   a cosmetic composition including an organic ultraviolet (UV) blocking component, wherein the cosmetic composition is impregnated in the foam, and
   wherein the polymer substrate for making the foam including the natural rubber (NR) and the hydrophobic polymer comprises between 5 wt % and 20 wt % of the natural rubber per the total weight of the polymer substrate.

2. The cosmetic according to claim 1, wherein the hydrophobic polymer is a polymer or copolymer of at least one selected from the group consisting of styrene, butadiene, chloroprene, acrylonitrile, isoprene, isobutylene, ethylene, and propylene.

3. The cosmetic according to claim 1, wherein the hydrophobic polymer is at least one selected from the group consisting of styrene-butadiene rubber (SBR), butadiene rubber (BR), acrylonitrile-butadiene rubber (NBR), acrylonitrile-butadiene-styrene (ABS), polyethylene (PE), polyvinyl alcohol (PVA), and ethylene vinyl acetate (EVA).

4. The cosmetic according to claim 1, wherein the organic UV blocking component is at least one selected from the group consisting of ethylhexylmethoxycinnamate, ethylhexylsalicylate, octocrylene, isoamyl-P-methoxycinnamate, butylmethoxydibenzoylmethane, homosalate, bis-ethylhexyloxyphenolmethoxyphenyltriazine, ethylhexyltriazone, diethylaminohydroxybenzoylhexylbenzoate, polysilicone-15 and paba(para-aminobenzoic acid), cinoxate, 4-methylbenzylidene camphor, glyceryl para-aminobenzoate, and ethylhexyl dimethyl paba.

5. The cosmetic according to claim 4, wherein the organic UV blocking component is ethylhexyl methoxycinnamate, ethylhexyl salicylate, octocrylene, or mixtures thereof.

6. The cosmetic according to claim 1, wherein the cosmetic composition is in water-in-oil type formulation.

\* \* \* \* \*